(12) United States Patent
Fisher

(10) Patent No.: US 9,638,670 B2
(45) Date of Patent: May 2, 2017

(54) INSPECTION SYSTEM FOR INSPECTING IN-SERVICE PIPING OR TUBING

(71) Applicant: BWXT Intech, Inc., Chattanooga, TN (US)

(72) Inventor: Benjamin D Fisher, Hixson, TN (US)

(73) Assignee: BWXT Intech, Inc., Chattanooga, TN (US)

( * ) Notice: Subject to any disclaimer, the term of this patent is extended or adjusted under 35 U.S.C. 154(b) by 139 days.

(21) Appl. No.: 14/695,497

(22) Filed: Apr. 24, 2015

(65) Prior Publication Data

US 2015/0308981 A1 Oct. 29, 2015

Related U.S. Application Data

(60) Provisional application No. 62/002,372, filed on May 23, 2014, provisional application No. 61/984,717, filed on Apr. 25, 2014.

(51) Int. Cl.
*G01N 29/04* (2006.01)
*G01N 29/265* (2006.01)

(52) U.S. Cl.
CPC .......... *G01N 29/04* (2013.01); *G01N 29/265* (2013.01); *G01N 2291/2634* (2013.01)

(58) Field of Classification Search
CPC ................ G01N 29/04; G01N 29/265; G01N 2291/2634
See application file for complete search history.

(56) References Cited

U.S. PATENT DOCUMENTS

| 2,427,129 | A | * | 9/1947 | Fields | B08B 9/023 |
| | | | | | 15/88 |
| 2,908,161 | A | * | 10/1959 | Bincer | G01N 29/26 |
| | | | | | 310/336 |
| 3,445,655 | A | * | 5/1969 | Curry | G01N 23/04 |
| | | | | | 378/171 |
| 3,602,036 | A | * | 8/1971 | Peterson | G01N 29/27 |
| | | | | | 73/633 |
| 3,765,229 | A | * | 10/1973 | Spencer | G01N 29/265 |
| | | | | | 73/640 |
| 3,776,179 | A | * | 12/1973 | Raney | B08B 9/0323 |
| | | | | | 118/306 |
| 3,921,440 | A | * | 11/1975 | Toth | G01N 29/265 |
| | | | | | 376/252 |
| 3,988,922 | A | * | 11/1976 | Clark | G01M 3/24 |
| | | | | | 367/104 |

(Continued)

*Primary Examiner* — David Bolduc
(74) *Attorney, Agent, or Firm* — Nelson Mullins Riley & Scarborough, LLP

(57) ABSTRACT

A pipe scanning apparatus includes a scanner collar fitted around the outside of a pipe with tools for inspecting or modifying the pipe, a tubular fabric pipe sheath fitted around the outside of the pipe and connected at an end to the scanner collar, and a powered winch or manually operable reel configured to draw in the tubular fabric pipe sheath so as to scan the scanner collar connected to the end of the tubular fabric pipe sheath over the pipe. The tubular fabric pipe sheath may include inelastic warp fibers running parallel with the pipe and elastic weft fibers running around the pipe. The pipe sheath may include at least one longitudinal slit with a slit fastener, and may include two such slits on opposite sides so that the pipe sheath is separable into two sheath halves.

25 Claims, 13 Drawing Sheets

(56) References Cited

U.S. PATENT DOCUMENTS

| | | | | |
|---|---|---|---|---|
| 4,331,034 A * | 5/1982 | Takeda | G01N 29/265 | 376/252 |
| 4,531,413 A * | 7/1985 | Tsuchita | B82Y 15/00 | 73/637 |
| 4,856,337 A * | 8/1989 | Metala | G01N 27/902 | 324/220 |
| 4,938,081 A * | 7/1990 | Negishi | F16L 55/28 | 73/865.8 |
| 4,955,235 A * | 9/1990 | Metala | G01N 27/902 | 324/226 |
| 4,995,320 A * | 2/1991 | Sato | B61B 13/04 | 104/118 |
| 5,028,381 A * | 7/1991 | Dugue | B23K 31/12 | 376/245 |
| 5,069,234 A * | 12/1991 | Nielsen | B08B 9/023 | 118/307 |
| 5,473,953 A * | 12/1995 | Appel | G01N 29/225 | 324/220 |
| 5,619,423 A * | 4/1997 | Scrantz | G01N 29/2412 | 324/220 |
| 5,698,799 A * | 12/1997 | Lee, Jr. | E21B 33/127 | 175/21 |
| 7,284,456 B2 * | 10/2007 | Lavoie | G01B 17/02 | 348/84 |
| 8,061,208 B2 * | 11/2011 | Roberts | G01N 27/90 | 73/622 |
| 9,389,150 B2 * | 7/2016 | Kimpel, Jr. | G01M 99/00 | |
| 2005/0041775 A1 * | 2/2005 | Batzinger | G01N 23/18 | 378/59 |
| 2006/0114002 A1 * | 6/2006 | Sukeda | G01N 29/0609 | 324/538 |
| 2009/0025490 A1 * | 1/2009 | Brandstrom | G01B 21/10 | 73/865.9 |
| 2009/0038398 A1 * | 2/2009 | Lavoie | G01N 29/225 | 73/637 |
| 2009/0120215 A1 * | 5/2009 | Jacobson | F17D 5/00 | 73/865.8 |
| 2009/0139337 A1 * | 6/2009 | Owens | G01N 29/2412 | 73/622 |
| 2009/0145249 A1 * | 6/2009 | Dubbeldam | G01D 11/30 | 73/866.5 |
| 2009/0314089 A1 * | 12/2009 | Brignac | G01N 29/226 | 73/622 |
| 2010/0275694 A1 * | 11/2010 | Roberts | F17D 5/00 | 73/637 |
| 2010/0326220 A1 * | 12/2010 | Dubbeldam | F16L 3/1066 | 73/865.8 |
| 2012/0033788 A1 * | 2/2012 | Kovarik | B66F 11/042 | 378/58 |
| 2012/0053856 A1 * | 3/2012 | Morrison, Jr. | G01N 29/262 | 702/39 |
| 2012/0204645 A1 * | 8/2012 | Crumpton | G01N 29/043 | 73/588 |
| 2013/0028377 A1 * | 1/2013 | Kovarik | B66F 11/042 | 378/59 |
| 2015/0300991 A1 * | 10/2015 | Sword | G01N 29/04 | 73/618 |

* cited by examiner

INSPECTION SYSTEM FOR INSPECTING IN-SERVICE PIPING OR TUBING

This application claims the benefit of U.S. Provisional Application No. 62/002,372 filed May 23, 2014 and entitled "Inspection System for Inspecting In-Service Piping or Tubing", and U.S. Provisional Application No. 61/984,717 filed Apr. 25, 2014 and entitled "Inspection System for Inspecting In-Service Piping or Tubing". U.S. Provisional Application No. 62/002,372 filed May 23, 2014 is incorporated herein by reference in its entirety. U.S. Provisional Application No. 61/984,717 filed Apr. 25, 2014 is incorporated herein by reference in its entirety.

BACKGROUND

The following pertains to the pipe or tube inspection arts, pipe or tube maintenance arts, industrial systems maintenance arts, and related arts.

Pipes or tubes (these terms being used interchangeably herein, along with variants such as piping or tubing) carry fluids for diverse purposes. As some non-limiting illustrative examples, steam pipes carry steam, water pipes carry water (possibly with various additives or so forth), pipes or tubes associated with a nuclear reactor may carry steam or water having some level of radioactive contamination, or may carry deuterium (e.g., a pressurized heavy water reactor, PHWR), gas pipes may carry hydrocarbon-based fluids such as natural gas, or in another context may carry process gases such as nitrogen or oxygen, and so forth. An illustrative example of a PHWR is the Canadian Deuterium Uranium (CANDU®) reactor. Fluids carried by industrial piping may be at elevated temperature and/or pressure (or conversely low temperature, e.g., liquid nitrogen, and/or low pressure, e.g., vacuum piping), may be transported at high flow rates, or otherwise may introduce stress to the pipes. Fluids carried by industrial piping may also introduce chemical stress, e.g., corrosion—for example, some nuclear reactors employ coolant water containing boric acid which serves as a soluble neutron poison.

The various fluids carried by industrial piping can damage the piping by various mechanisms, including high flow velocity-related damage, chemical damage (e.g., in piping carrying corrosive fluid), radiation damage (e.g., in piping carrying fluid contaminated with radiation), or so forth. Damage tends to be more extensive at pipe bends and at welds between pipe segments. In view of these concerns, pipe inspection is common industrial practice, and may be mandated by applicable governmental regulations, for example in the nuclear industry.

However, pipe inspection is challenging due to the typically long lengths of piping that need to be inspected, and the need to inspect pipe bends, weld joints, or other features some of which may not be readily accessible. Additionally, industrial piping is sometimes arranged in a densely packed layout, with pipes sometimes passing within close proximity to one another, again limiting access for inspection.

A known approach for pipe inspection employs an inspection head that includes suitable sensing elements, such as an ultrasonic testing (UT) inspection head, radiographic inspection head, eddy current inspection head, or so forth, that is inserted into the pipe and pushed or drawn through the pipe using a snake, cable, or the like. These approaches require access to the pipe interior, and therefore cannot be used to inspect piping during operation (that is, when the piping is carrying working fluid). Another consideration is that the rotational orientation of the inspection head inside the pipe, as well as its position along the pipe, usually must be known or tracked as the inspection head moves through the interior of the pipe. This may be addressed by suitable spatial encoding of the inspection head position, for example based on the rotation of driving wheels of a robotic apparatus, but any slippage of the spatial encoding mechanism during the inspection can lead to spatial encoding errors.

An illustrative example of a difficult pipe inspection task is the inspection of feeder pipes in a CANDU® heavy water nuclear reactor. In this heavy water reactor the radioactive core is arranged as an array of mutually parallel horizontally oriented fuel tubes. Each fuel tube contains a fuel bundle comprising a fissile material such as uranium with low $^{235}$U enrichment (or no enrichment at all) or mixed oxide fuel (MOX fuel). To achieve critical mass for the nuclear chain reaction, the fuel tubes must be spaced closely together in a relatively tight array. Feeder pipes carry primary (deuterium) coolant to these closely spaced fuel tubes, and the density of feeder pipes near their connections with the fuel tubes is high, with feeder pipes passing within close proximity to one another and including various bends in order to fit all the feeder pipes into the limited available space. By way of illustrative example, some Candu® reactors include 480 fuel tubes fed by 480 inlet feeder pipes and 480 outlet feeder pipes. The feeder pipes are prone to corrosion over time due to the continual flow of radioactive deuterium coolant, especially at feeder bends and at pipe segment welds (although corrosion can occur elsewhere and the pipe inspection typically inspects both tight and large-radius bends as well as straight sections). A break in a feeder pipe due to such corrosion constitutes a loss of coolant accident (LOCA) producing a radiological release into the surrounding containment structure, and may require immediate shutdown of the nuclear reactor and extensive post-shutdown cleanup and incident analysis before the reactor can be brought back online. Consequently, governing nuclear regulations in the United States, Canada, and some other jurisdictions require periodic inspection of all feeder pipes to detect any thinned pipe regions. It is preferable to perform such inspections without accessing the interior of the pipe. For example, during a typical CANDU® feeder pipe inspection process, only one feeder pipe per reactor can be isolated with a liquid nitrogen freeze plug (as no valves are available on the feeder pipes), and drained at a time per the regulator authority. Such a process would also limit productivity if the inspection were done from the ID. Feeder pipe inspection is further complicated by high radioactivity levels in the vicinity of the reactor core which limits access to the feeder pipes by plant operators. In a typical inspection procedure, a technician approaches the reactor core in a radiation-shielded trolley or cart (RDP platform), and performs inspection operations through slits provided by panel shielding curtains. Even with these precautions, the technician's exposure time to radioactivity proximate to the reactor core limits the time for performing the inspection in accord with radiation exposure limits that apply to all nuclear plant operators.

A known approach for performing CANDU® reactor feeder pipe inspection uses an inspection ring that is driven along the outside diameter of the feeder pipe by a robotic crawler. However, this approach has been prone to slippage which introduces spatial encoding errors, and the robotic crawler can exhibit difficulty crawling over sharp pipe bends or welds that protrude from the pipe's exterior surface. Improvements might be obtained by using more complex robotic crawlers (e.g., a multiple-axis robotic arm), but at commensurate increase in robotics manufacturing cost as well as increased likelihood of breakdown in the field due to the increased robotic complexity, and possibly increased setup time leading to increased radiation exposure for the technician.

While CANDU® reactor feeder pipe inspection is described herein as an illustrative example of a difficult pipe inspection task, it will be appreciated that similar problems may arise in any piping inspection task in which the piping is to be inspected while in-service (or in which the pipe interior is otherwise inaccessible, for example due to corrosive residue deposits inside the pipe). There remains an unfulfilled need for improved pipe inspection apparatus of low cost and high reliability that can inspect in-service piping, maintain accurate position encoding in both axial and rotational orientations, and provide other benefits.

BRIEF SUMMARY

In some embodiments described herein as illustrative examples, an apparatus for scanning a pipe comprises: a scanner collar sized to fit around the outside of the pipe and including tools configured to inspect or modify the pipe; a tubular fabric pipe sheath sized to fit around the outside of the pipe and connected at an end to the scanner collar; and a powered winch or manually operable reel configured to draw in the tubular fabric pipe sheath so as to scan the scanner collar connected to the end of the tubular fabric pipe sheath over the pipe. The tubular fabric pipe sheath may include warp fibers arranged to run parallel with the pipe when the tubular fabric pipe sheath is fitted around the outside of the pipe, and weft fibers arranged to run at least partway around the pipe when the tubular fabric pipe sheath is fitted around the outside of the pipe. The weft fibers are more elastic than the warp fibers, and in some embodiments the warp fibers are inelastic and the weft fibers are elastic. The tubular fabric pipe sheath preferably includes at least one longitudinal slit having a slit fastener, and in some embodiments includes two such longitudinal slits on opposite sides of the tubular fabric pipe sheath whereby the tubular fabric pipe sheath is separable into two sheath halves. More generally, the tubular fabric pipe sheath is more elastic in its circumferential direction than in its axial direction, and in some embodiments is inelastic in its axial direction and elastic in its circumferential direction. The apparatus may further comprise an unfastening element disposed with the powered winch or manually operable reel, which is configured to open the one or more slit fasteners as the tubular fabric pipe sheath is drawn into the powered winch or manually operable reel. The tools of the scanner collar may include one or more of: ultrasonic testing (UT) sensors, radiographic inspection sensors, eddy current inspection sensors, a pipe welding tool, a pipe surface coating tool, and a pipe sanding tool.

In some embodiments described herein as illustrative examples, an apparatus for scanning a pipe comprises a scanner collar sized to fit around the outside of the pipe and including tools configured to inspect or modify the pipe, and a tubular fabric pipe sheath sized to fit around the outside of the pipe and connected at an end to the scanner collar. The tubular fabric pipe sheath includes warp and weft fibers. The warp fibers run along the tube axis of the tubular fabric pipe sheath. The tubular fabric pipe sheath further includes at least one longitudinal slit having a slit fastener. The weft fibers are more elastic than the warp fibers, and in some embodiments the warp fibers are inelastic and the weft fibers are elastic. In one embodiment the tubular fabric pipe sheath includes two longitudinal slits on opposite sides of the tubular fabric pipe sheath whereby the tubular fabric pipe sheath is separable into two sheath halves. The apparatus may further comprise a powered winch or manually operable reel configured to draw in the tubular fabric pipe sheath so as to scan the scanner collar connected to the end of the tubular fabric pipe sheath over the pipe. For some pipe inspection tasks, the scanner collar is a pipe inspection collar and the tools of the pipe inspection collar include one or more of ultrasonic testing (UT) sensors, radiographic inspection sensors, and eddy current inspection sensors. The apparatus may further include sanding belts configured to sand the outside of the pipe, wherein the rotational direction of the sanding belts is effective to apply a force to the scanner collar in a direction opposite the drawing force applied by the powered winch or manually operable reel.

In some embodiments described herein as illustrative examples, a method for scanning a pipe comprises: moving a scanner collar secured around the outside of the pipe to an outboard position, the moving causing a tubular fabric pipe sheath connected to the scanner collar to extend and sheath the pipe up to the outboard position of the scanner collar; drawing the tubular fabric pipe sheath inward, the drawing causing the scanner collar to move inward from its initial outboard position; and, during the drawing, operating tools disposed on the scanner collar to inspect or modify the pipe. The drawing of the tubular fabric pipe sheath may use a powered winch or manually operable reel, and as the tubular fabric pipe sheath reaches the powered winch or manually operable reel, one or more longitudinal seams of the tubular fabric pipe sheath are separated to disengage the tubular fabric pipe sheath from the pipe. In some embodiments the method does not include accessing the interior of the pipe. In some embodiments, the moving comprises operating sanding belts mounted on or with the scanner collar to sand the outside of the pipe, the engagement of the sanding belts with the outside of the pipe also moving the scanner collar toward the outboard position.

These and other non-limiting aspects and/or objects of the disclosure are more particularly described below.

BRIEF DESCRIPTION OF THE DRAWINGS

The invention may take form in various components and arrangements of components, and in various process operations and arrangements of process operations. The drawings are only for purposes of illustrating preferred embodiments and are not to be construed as limiting the invention. This disclosure includes the following drawings.

DETAILED DESCRIPTION OF THE PREFERRED EMBODIMENTS

Figure 1:
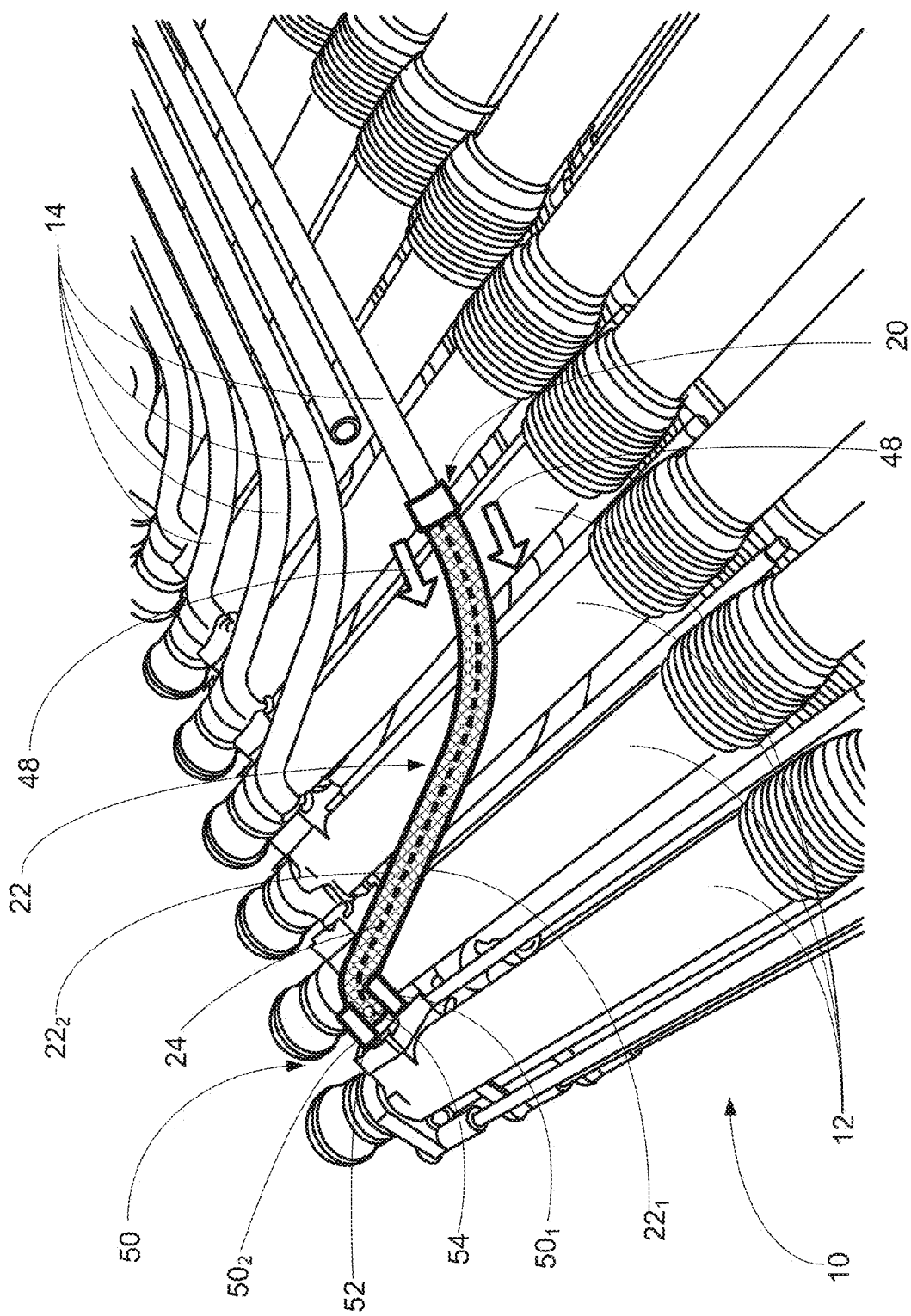
FIGS. 1-4 diagrammatically show alternative perspective views of a pipe scanning apparatus as disclosed herein, with a scanner collar of the pipe scanning apparatus shown in the upper inset of FIG. 4.

A more complete understanding of the processes and apparatuses disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

A value modified by a term or terms, such as "about" and "substantially," may not be limited to the precise value specified.

It should be noted that many of the terms used herein are relative terms. For example, the terms "interior", "exterior", "inward", and "outward" are relative to a center, and should not be construed as requiring a particular orientation or location of the structure.

To the extent that explanations of certain terminology or principles of the pipe or tube inspection arts, pipe or tube maintenance arts, industrial systems maintenance arts, and related arts may be necessary to understand the present disclosure, the reader is referred to Steam/its generation and use, 40th Edition, Stultz and Kitto, Eds., Copyright 1992, The Babcock & Wilcox Company, and to Steam/its generation and use, 41st Edition, Kitto and Stultz, Eds., Copyright 2005, The Babcock & Wilcox Company, the texts of which are hereby incorporated by reference as though fully set forth herein.

Disclosed herein are improved pipe inspection techniques that do not require access to the pipe interior (although they may be employed to inspect pipes whose interior is accessible) and provide improved pipe inspection apparatus of low cost and high reliability that can inspect in-service piping, maintain accurate position encoding in both axial and rotational orientations, provide rapid inspection apparatus setup time, and provide other benefits. In the following, the pipe inspection techniques are disclosed in conjunction with the illustrative CANDU® reactor feeder pipe inspection task; however, it is to be understood that the disclosed improved pipe inspection techniques are applicable for performing diverse pipe inspection tasks including inspection of steam pipes, water pipes, gas pipes, or substantially any other type of pipe carrying (or designed to carry) substantially any type of working fluid. Further, the disclosed pipe inspection techniques may be applied to inspect pipe inner and/or outer surfaces, pipe welds, pipe bends, pipe coatings, or substantially any other pipe feature of interest for inspection. The disclosed inspection techniques advantageously can be applied to inspect in-service piping (that is, piping that is carrying working fluid or whose interior is otherwise inaccessible), but also can be applied to inspect piping that is out of service or whose pipe interior is otherwise accessible. Still further, while the application of pipe inspection is described, more generally the techniques disclosed herein provide improved mechanisms for moving a scanner collar (e.g., inspection collar) along a pipe, and may find application in pipe inspection, pipe maintenance (e.g., applying a controlled coating to the pipe exterior), pipe welding (e.g., moving to a precise spot identified by scanner collar-mounted sensors and applying a weld using a scanner collar-mounted welding tool), or so forth.

With reference to FIG. 1, a portion of an illustrative CANDU® heavy nuclear reactor core 10 is shown in perspective view, including an array of mutually parallel horizontally oriented fuel tubes 12. The view of the reactor core 10 shown in FIG. 1 includes only first ends of the fuel tubes 12, into which inlet feeder pipes 14 flow deuterium which serves as the primary coolant. At the second ends (not shown) of the fuel tubes a similar set of outlet feeder pipes flows deuterium out of the fuel tubes. Both the input feeder pipes 14 and the outlet feeder pipes are typically inspected on a periodic basis, and the inspection techniques are described herein with illustrative reference to the inlet feeder pipes 14. Each fuel tube 12 contains internal components (not shown) including a fuel bundle typically made up of a bundle of rods containing a uranium compound (e.g., $UO_2$) at its natural fissile $^{235}U$ isotope concentration of about 0.7%, or optionally having some (typically low) level of $^{235}U$ enrichment such that the concentration is greater than 0.7%. Alternatively, the fuel may be MOX fuel or some other fissile material. FIG. 1 and other drawings herein illustrate a few representative fuel tubes 12, but more generally the Candu® reactor typically includes a larger array of mutually parallel horizontally oriented fuel tubes, for example arranged as a square array with "rounded" corners so as to approximate a cylindrical reactor core of horizontal length defined by the length of the fuel tubes 12 and cross-sectional area defined by the arrangement of the fuel tubes 12 making up the core. By way of illustrative example, some Candu® reactors include 480 fuel tubes 12 fed by 480 inlet feeder pipes 14 (and further having a corresponding 480 outlet feeder pipes at the opposite ends of the fuel tubes 12). More generally, the number of feeder tubes 12, their spacing, the contained fissile material, and other characteristics are chosen to provide desired thermal heat generation and other core characteristics. It is also to be appreciated that Candu® heavy water reactors typically include various additional conventional components not illustrated in the drawings herein, such as control rod apparatus, piping leading to external steam generators, a surrounding radiological containment, fueling machinery, pumps, and so forth.

Figure 2:
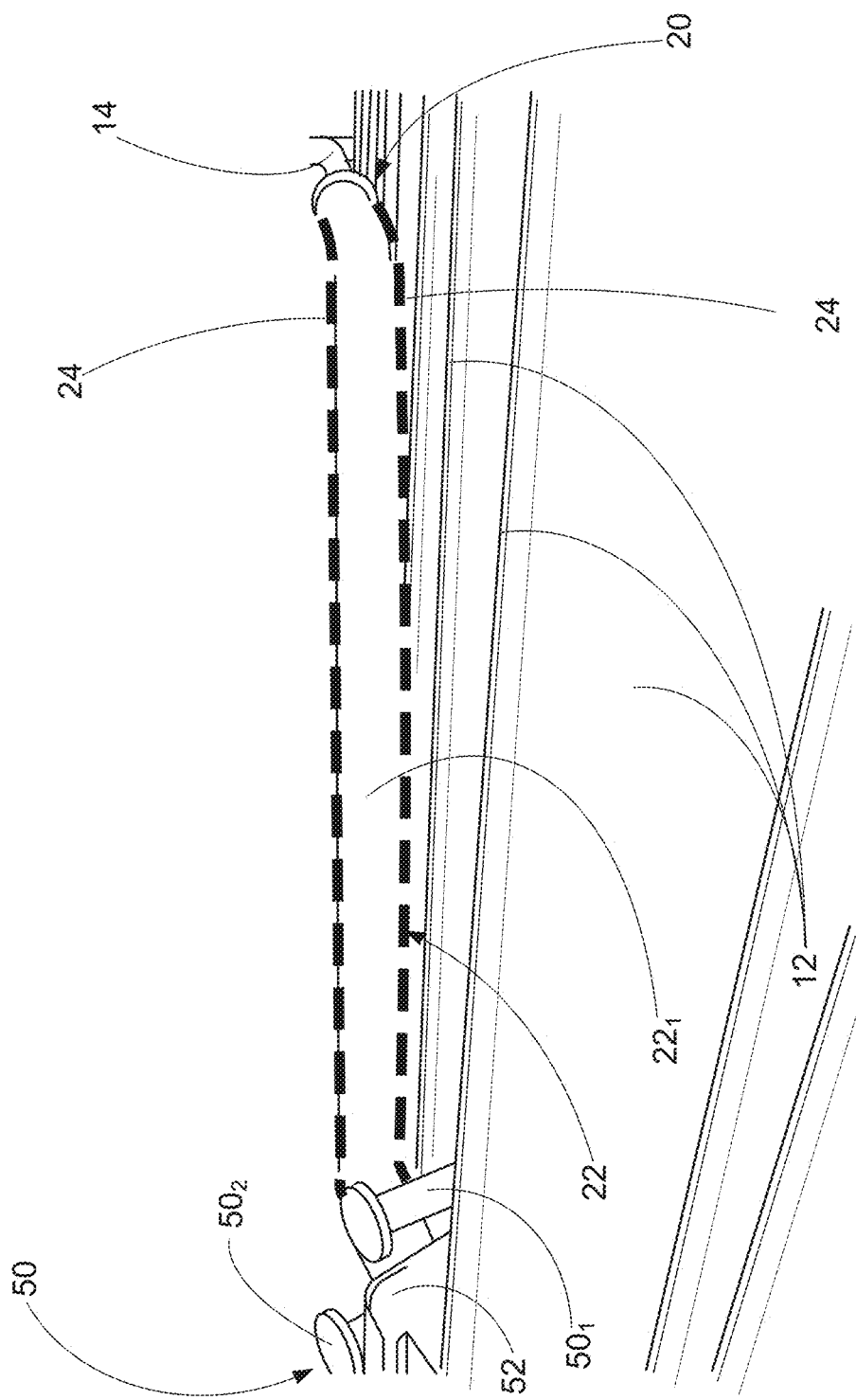
Figure 3:
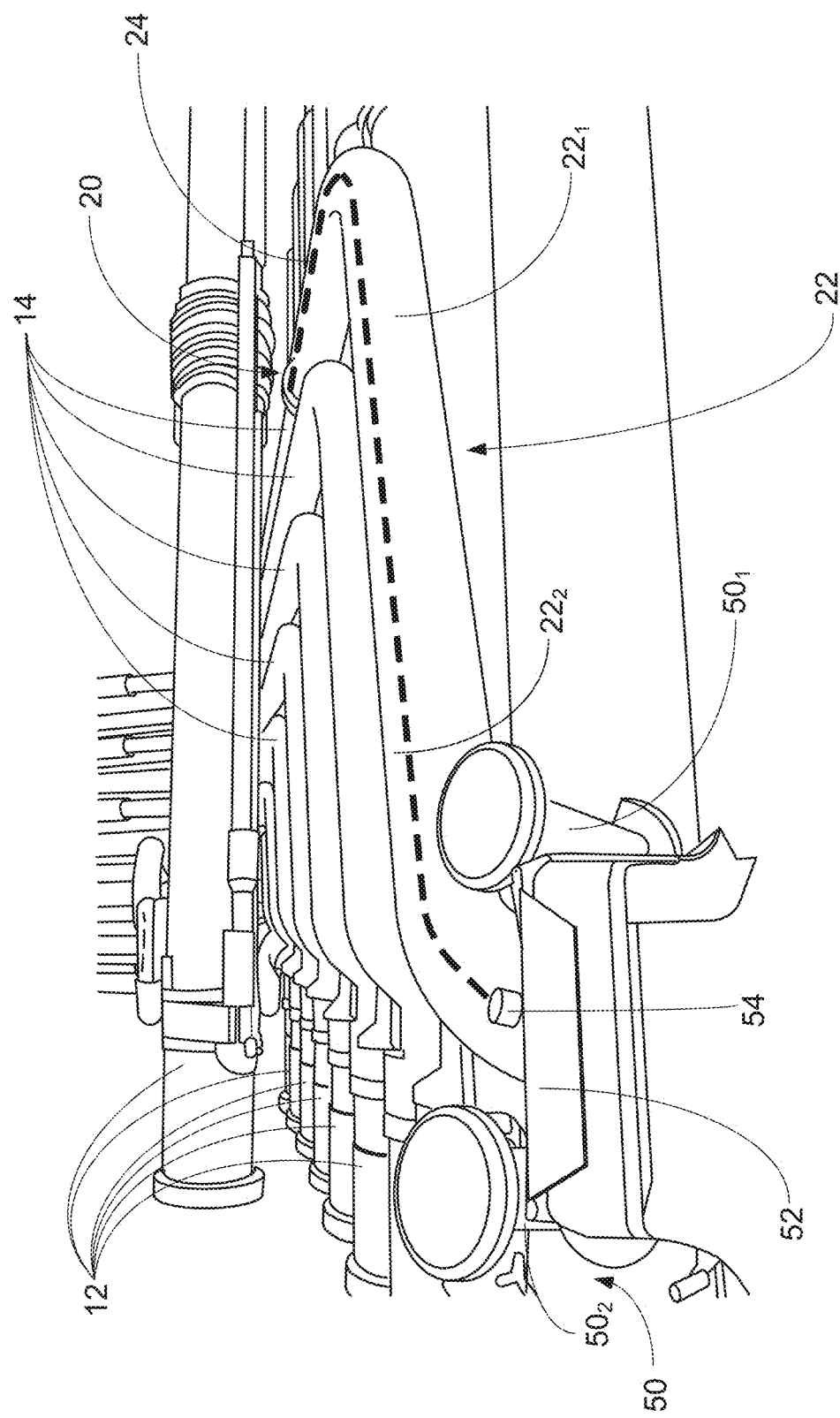
Figure 4:
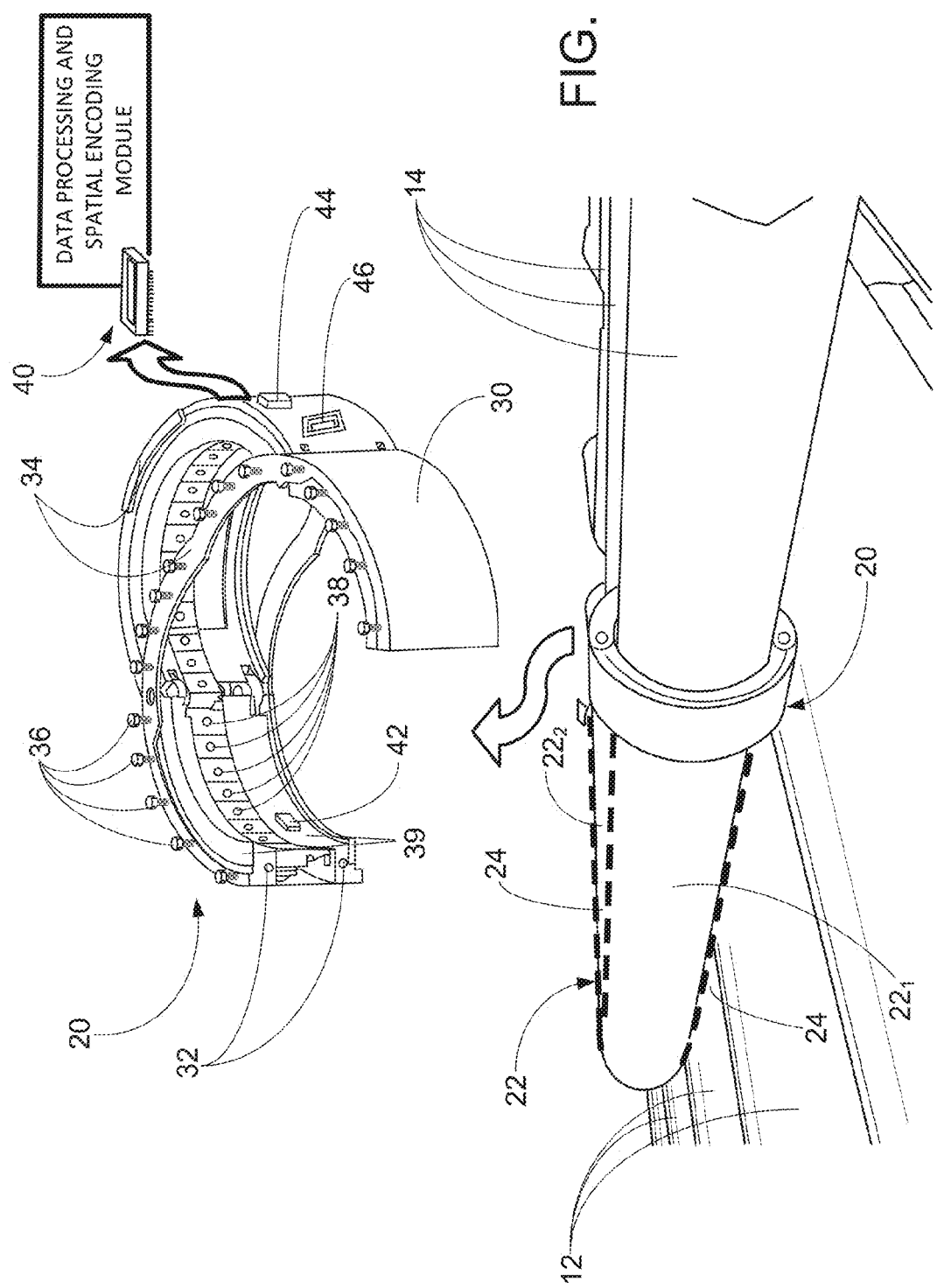

With continuing reference to FIG. 1 and with further reference to FIGS. 2-4, a feeder pipe inspection apparatus includes a scanner collar 20 disposed at the end of a tubular fabric pipe sheath 22. To enable the sheath 22 to be fitted around the pipe 14, it preferably includes at least one longitudinal slit, which is suitably after being fitted onto the pipe 14 by a slit fastener 24. In the illustrative example, the tubular fabric pipe sheath 22 includes two longitudinal slits on opposite sides of the sheath 22 and two corresponding slit fasteners 24, so that the tubular fabric pipe sheath 22 is separable into two sheath halves $22_1$, $22_2$ each running halfway around the pipe 14. The slit fastener(s) 24 may be zippers, hook-and-loop strips (e.g., Velcro strips), buttons, snaps, or the like.

With particular reference to FIG. 4, an illustrative embodiment of the scanner collar 20 is shown in the upper inset comprises a segmented clamp-on collar body 30 that clamps onto the pipe 14, and includes magnetic locking/unlocking features 32, 34. More generally, the scanner collar can employ any collar body capable of being fitted around the pipe—as another example, the scanner collar body can comprise two separate halves that snap together around the pipe. The illustrative scanner body 30 includes posts 36 via which the tubular fabric pipe sheath 22 is connected to the scanner collar 20. Instead of illustrative posts 36, another type of connector or securing mechanism can be employed. The scanner collar body 30 supports tools 38 configured to inspect or modify the pipe 14. For the illustrative Candu® feeder pipe inspection task, the tools 38 suitably comprise ultrasonic testing (UT) sensors (preferably although not necessarily configured as a phased-array UT pipe probe), although other types of testing sensors are contemplated such as radiographic inspection sensors, eddy current inspection sensors, or so forth. The illustrative scanner collar 20 further includes optional peripheral annular flanges 39 that space the UT sensors 38 away from the pipe surface when the collar 20 is clamped onto the pipe, so as to define a small gap that can be filled with fluid (e.g., water) to provide a fluid interface for the UT sensors 38. For performing maintenance tasks, the tools 38 may include a pipe welding tool, a pipe surface coating tool, or so forth, instead of or in addition to pipe inspection sensors. The illustrative scanner collar 20 includes on-board electronic data processing comprising a microprocessor or microcontroller 40 (shown outside of the collar body 30 for illustrative purposes, but typically mounted on or inside the collar body 30, or alternatively may be located remotely and connected with the collar via an RS232 cable or other wired or wireless communication link). The microprocessor or microcontroller 40 is programmed to read data from the sensors 38, for example using discrete analog-to-digital (A/D) circuits, not shown, or A/D circuitry built into the microchip or microcontroller 40. If welding or coating tools are provided on the scanner collar, the microprocessor or microcontroller 40 is suitably programmed to operate these tools. The microprocessor or microcontroller 40 is also configured to perform spatial encoding of the scanner collar 20 as it scans over the pipe 14, for example by reading an axial position sensor 42 which may for example be embodied as an optical (e.g., semiconductor laser-based) sensor that detects movement of the pipe 14 relative to the scanned collar 20, or alternatively may be a wheel-based movement sensor or so forth. In some embodiments it is desirable or necessary to track the rotational position of the scanner collar 20 during the scanning—this may be done, by way of illustrative example, by reading an on-board accelerometer 44 (preferably with six degrees of freedom, i.e. 6 DOF) or other sensor to detect changes in angular position of the scanner collar 20. Not shown in FIG. 4 is suitable wiring on or in the collar body 30 to operatively electrically interconnect the various components 38, 40, 42, 44. Such wiring may comprise discrete wires, small circuit boards, or so forth. Data from the sensors 38, and the spatial encoding computed based on readings of the position sensors 42, 44 is suitably stored in a non-volatile memory of the microchip or microcontroller 40 (or in a separate memory chip, not shown, that is operatively connected with the microchip or microcontroller 40) and may be read out after the scan via a USB port 46.

It should be appreciated that the illustrative scanner collar 20 shown in FIG. 4 is merely an illustrative example, and numerous variants are contemplated. The on-board electronic data processing and communications capabilities of the scanner collar can vary widely. For example, the scanner collar electronics may in some embodiments be limited to collecting raw sensor data and offloading the collected sensor data via electrical conductors running through the tubular fabric pipe sheath 22. Alternatively, the scanner collar electronics can include wireless communication capability (e.g., Bluetooth™) for offloading the collected sensor data. In these embodiments, computing the spatial encoding of the scanner collar is done at a separate computer that receives the offloaded sensor data. In such embodiments, the on-collar axial position sensor 42 is optionally omitted and the axial position computed based on the portion of the tubular fabric pipe sheath 22 drawn in during scanning (operation described elsewhere herein; this approach can also be used if axial position encoding is performed on the scanner collar 20 if the sheath draw information is provided to the microchip or microcontroller 40). In another variant embodiment, it is contemplated to include no electronic data processing capability at all at the scanner collar, and to instead offload the raw sensor data directly via electrical conductors running through the tubular fabric pipe sheath 22. In another contemplated variant, an array of (e.g., 6) linear phased array sensors arranged along the axis of the pipe with a rotation collar system that rotates (e.g., 60° or more) may be used. This axial orientation facilitates observation under weld caps. Use of a number of segments, such as 6 segments, increases the scan speed per altitude location along the pipe, and is faster than a full 360° scan. As yet another contemplated variant (not shown), the ring of inspection sensors 38 (e.g., UT sensors) is replaced by a single sensor (or other tool) and a rotatable sub-collar that rotates the sensor around the circumference of the pipe.

With reference back to FIGS. 1-3, in operation the scanner collar 20 is initially positioned at an outboard position along the pipe 14 to be inspected, as shown in FIGS. 1-3, and is then drawn toward an inboard position using the connected tubular fabric pipe sheath 22 (arrows 48 in FIG. 1 diagrammatically indicate the direction of movement applied to the scanner collar 20), with the pipe 14 being inspected (or processed) by the tools 38 of the scanner collar 20 as the scanner collar 20 is moved or drawn in from its initial outboard position. To apply the force providing the inward movement 48, the feeder pipe inspection apparatus further includes a powered winch or hand-operable reel 50 (hereinafter referred to generically as winch 50) positioned at the inboard position, so that operation of the winch 50 draws the scanner collar 20 from its initial outboard position inward along the (exterior of the) pipe toward the inboard position where the winch 50 is located. As the tubular fabric pipe sheath 22 reaches the winch 50, the slit fastener(s) 24 are opened and the two halves $24_1$, $24_2$ of the tubular fabric pipe sheath 24 are suitably collected on two respective spools $50_1$, $50_2$. (In an alternative embodiment in which the tubular fabric pipe sheath has only one longitudinal slit, a single spool is suitably used to collect the sheath after the slit fastener is undone). The winch 50 is mounted on a pipe flange 52 as illustrated, or on another suitably sturdy support element near the inboard end of the pipe 14, so as to provide a sturdy base from which to exert the pulling force on the tubular fabric pipe sheath 22. At the winch 50, the fastener(s) are undone, e.g., unzipped in the case of a zipper fastener, or pulled apart in the case of a hook-and-loop fastening strip, in order to enable the tubular fabric pipe sheath 22 to be removed from the pipe 14 under inspection at its inboard end. In some embodiments the slit fastener(s) 24 are undone manually; in the illustrative embodiment an unfastening element 54 disposed with the winch 50 is configured to open the slit fastener(s) 24 as the tubular fabric pipe sheath 22 is drawn into the winch 50. It will be appreciated that the rate or length of uptake of the tubular fabric pipe sheath 22 onto the spools $50_1$, $50_2$ provides an additional or alternative measure of the scanning speed or distance of the scanning collar 20. In view of this, it is contemplated to include a positional scanning sensor to measure uptake of the tubular fabric pipe sheath 22. For example, an optical or other type of position sensor (not shown, but suitably similar to the axial position sensor 42 mounted on the scanner collar 20) is contemplated to be mounted just before the infeed rollers to the spools $50_1$, $50_2$, and arranged to look directly at the fabric surface and calculate displacement of the fabric as it was reeled in. The texture of the woven fabric of the sheath 22 facilitates the displacement calculation, providing linear results with good reliability. Another contemplated approach is to provide rotary encoders on the spools $50_1$, $50_2$, or on idler in-feed rollers (not shown) located before the spools $50_1$, $50_2$. Mounting rotary encoders on in-feed rollers has the advantage of being non-powered, which is expected to increase sensitivity and accuracy. Another advantage of mounting on in-feed rollers is that the encoding of the spool with respect to the in-feed of fabric would need to take into account the increasing diameter of the spool and portion of rolled-up fabric, as this diameter will increase during uptake as more fabric is rolled up on the spools $50_1$, $50_2$. This correction for wrapped fabric may be difficult to perform accurately as there may be some compression of the fabric as it is wrapped onto the spools $50_1$, $50_2$. Since the amount of fabric taken up onto each of the spools $50_1$, $50_2$ should be the same, it is contemplated to measure uptake onto each of the spools $50_1$, $50_2$ and take the average and/or record both values as a further quality control check.

Figure 5:
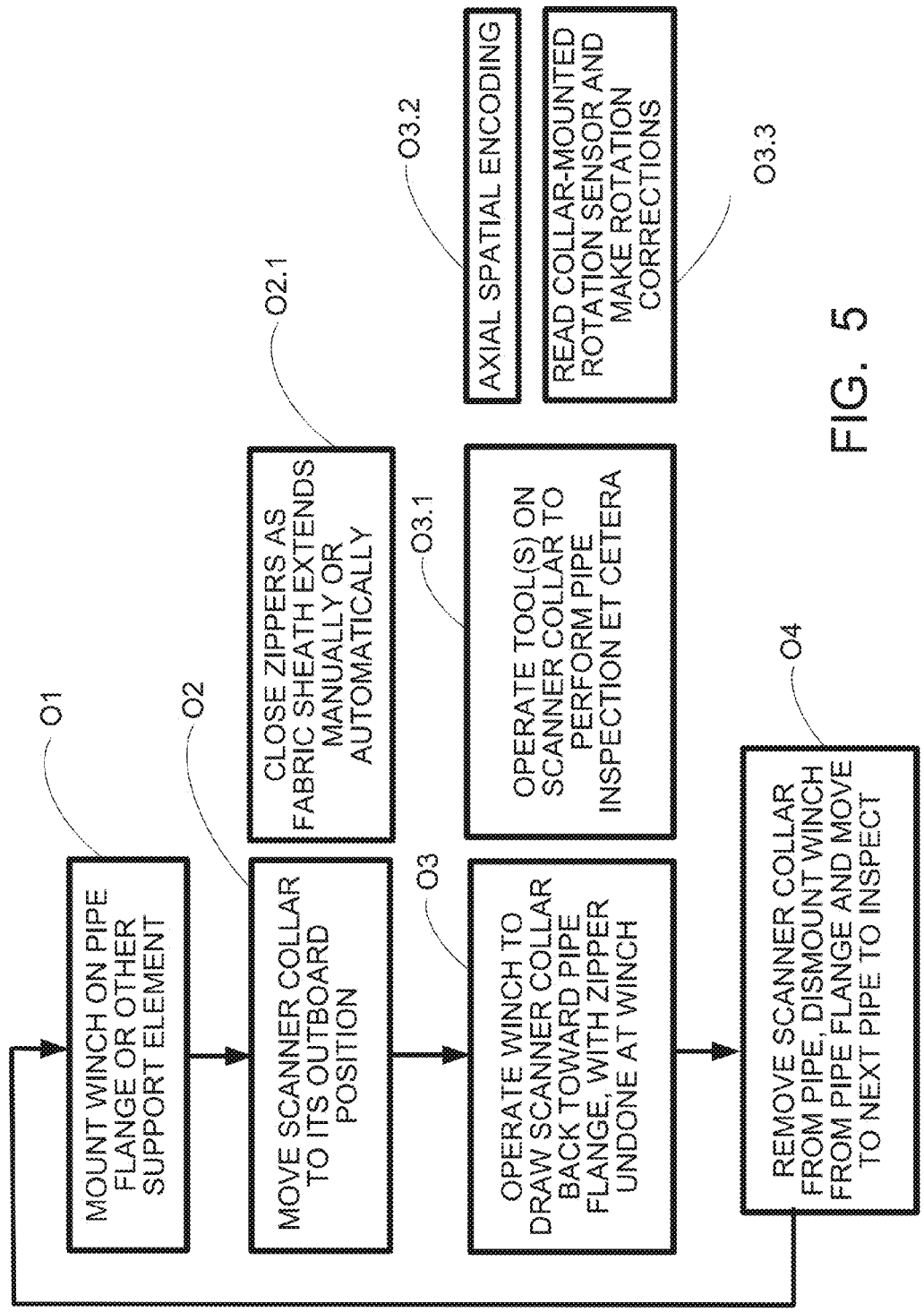
FIG. 5 diagrammatically shows a pipe inspection process suitably performed using the pipe scanning apparatus of FIGS. 1-4.

With continuing reference to FIGS. 1-4 and with further reference to FIG. 5, a pipe inspection process is described, which is suitably performed using the pipe scanning apparatus of FIGS. 1-4. In an operation O1, the winch 50 is mounted on the pipe flange 52 or other support element proximate to the inboard end of the pipe 14 to be inspected. In an operation O2, the optional unfastening element 54 is also suitably mounted. In an operation O2, the scanner collar 20 is moved to its outboard position. This can be done in various ways, depending upon accessibility of the exterior of the pipe 14 to be inspected. If the pipe is easily accessible then this can be done by fitting the scanner collar onto the pipe at its outboard position, fitting the tubular fabric pipe sheath around the pipe and fastening the slit fastener(s). However, in the illustrative Candu® feeder pipe inspection task, access to the outboard position along the pipe 14 is limited both by the close packing of the feeder pipes 14 proximate to the nuclear reactor core 10 and also by high radioactivity levels that do not permit nuclear plant operators access inside the reactor core 10 (or, more precisely, in the inter-fuel channel area which is proximate to the Candu® reactor core). For this task, a suitable approach is to fit the scanner collar 20 onto the pipe 14 to be inspected at its inboard position (that is, close to the winch 50), and then moving the scanner collar 20 along the pipe 14 using a stick or other element until the scanner collar 20 reaches its outboard position. As the scanner collar 20 is moved out, the tubular fabric pipe sheath 22 is suitably unrolled off the spools $50_1$, $50_2$ onto the pipe 14 and the slit fasteners 24 fastened together (operation O2.1 of FIG. 5) as the tubular fabric pipe sheath 22 is unrolled in order to fit it around the pipe 14. Note that the pipe is not being scanned or processed by the scanner collar 20 during the operation O2—in view of this, another contemplated approach is to employ an outboard towing motor (not shown) mounted on the scanner collar or connected to tow the scanner collar along the pipe to its outboard position. Since no scanning or spatial encoding is performed during the trip outboard, the towing motor can be a coarse device designed for torque rather than precision.

The pipe scanning is performed in an operation O3 indicated in FIG. 5 in which the winch 50 is operated to draw the scanner collar 20 back toward the pipe flange 52 (inboard position). As the tubular fabric pipe sheath 22 reaches the winch, the zipper or other slit fastener(s) 24 is undone by the unfastening element 54 or manually so that the tubular fabric pipe sheath 22 can be removed from the pipe 14 and collected on the spools $50_1$, $50_2$. During the drawing of the scanner collar 20 toward its inboard position, the tool(s) 38 on the scanner collar 20 are operated to perform pipe inspection or other pipe scanning such as welding or coating (operation O3.1 of FIG. 5). Additionally, and also during the drawing of the scanner collar 20 toward its inboard position, the spatial encoding of the scanner collar 20 is performed (axial encoding operation O3.2 and optional rotational encoding operation O3.3). The axial encoding operation O3.2 can be performed based on information provided by the axial position sensor 42 optionally mounted on the scanner collar 20, or can be performed based on the length of the tubular fabric pipe sheath 22 taken up on the spools $50_1$, $50_2$ (where the axial distance through which the scanner collar 20 moves is equal to the length of tubular fabric pipe sheath 22 taken up on the spools). The optional rotational encoding operation O3.3 is suitably performed based on readings of the on-board accelerometer 44 or other rotational sensor. It will be appreciated that the spatial encoding operations O3.2, O3.3 may be performed on-board by the microchip or microcontroller 40 or off-board by a separate computer, or various combinations of on-board and off-board processing may be employed. After the pipe scan is complete, the scanner collar 20 has been drawn back to its inboard position proximate to the winch 50. At this point, in an operation O4 the scanner collar 20 is removed from the pipe 14 which has just been inspected, the winch 50 is dismounted from the pipe flange 54, and the pipe scanning apparatus is moved to the next feeder pipe to be inspected starting again with operation O1. Advantageously, at the point in time of operation O4 the scanner collar 20 is in its inboard position so its removal entails limited radiation exposure to the plant operator who performs this task. The operation O4 optionally also includes reading data off the scanner collar 20 using the on-board USB port 46. (Depending on the amount of on-board non-volatile memory available on the scanner collar 20 this may only need to be done after scanning several pipes, or if wireless communication is used the data may be offloaded continuously during the scanning operation O3 so that no on-board data storage is needed on the collar).

In the foregoing pipe scanning apparatus and processing, the spatial position of the scanner collar 20 is suitably spatially encoded based on position sensor readings. However, if the axial position is inferred from the length of the tubular fabric pipe sheath 22 taken up on the spools $50_1$, $50_2$, then any elasticity (i.e. stretchiness) of the tubular fabric pipe sheath 22 along its tube axis direction will generally lead to axial encoding error. However, elasticity of the tubular fabric pipe sheath 22 is useful to enable the scanner collar 20 to be drawn over pipe bends, pipe welds, or the like.

Figure 6:
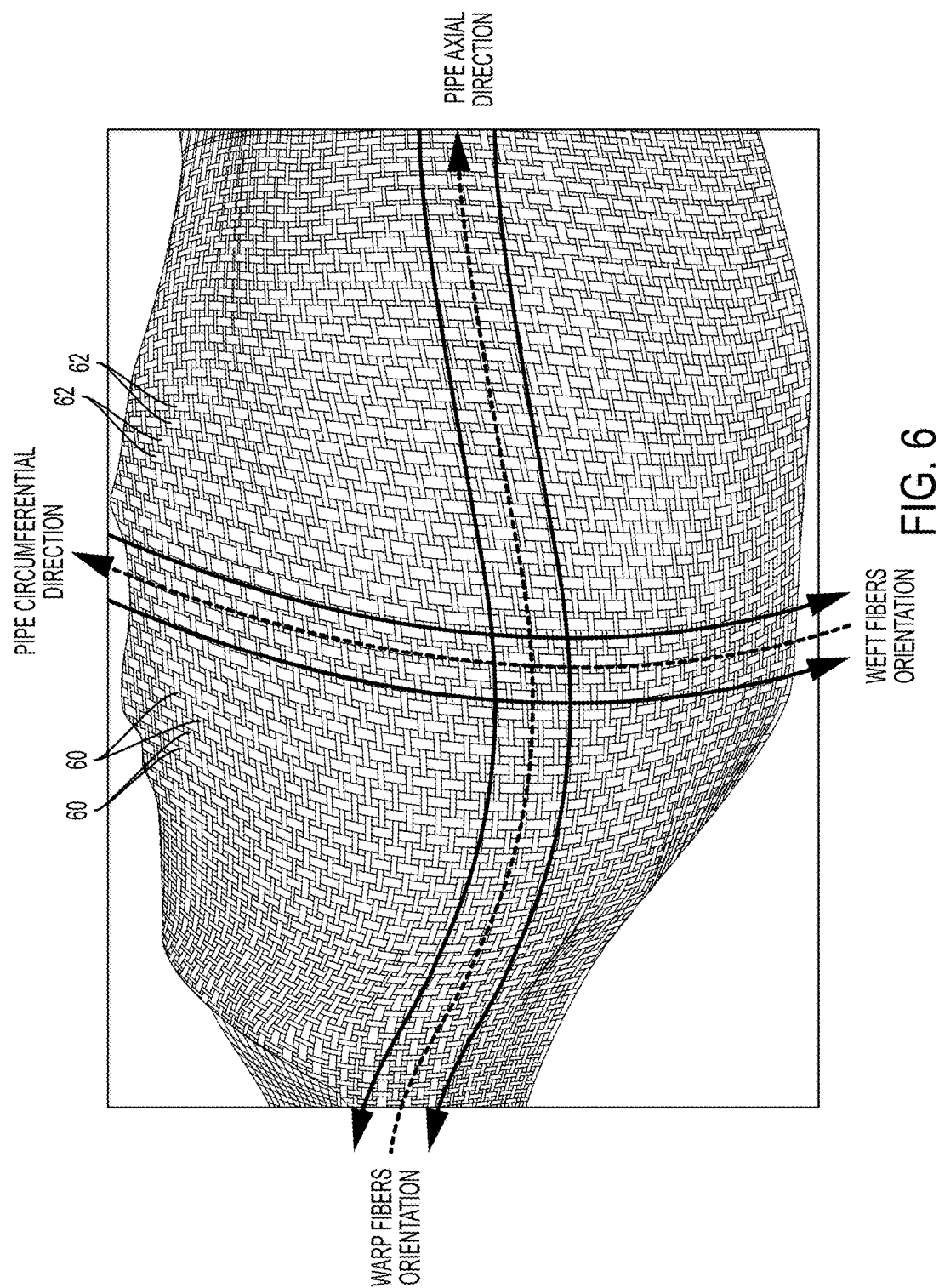
FIGS. 6 and 7 diagrammatically show an illustrative embodiment of the tubular fabric pipe sheath of the pipe scanning apparatus of FIGS. 1-4, including illustrative warp and weft fibers.
Figure 7:
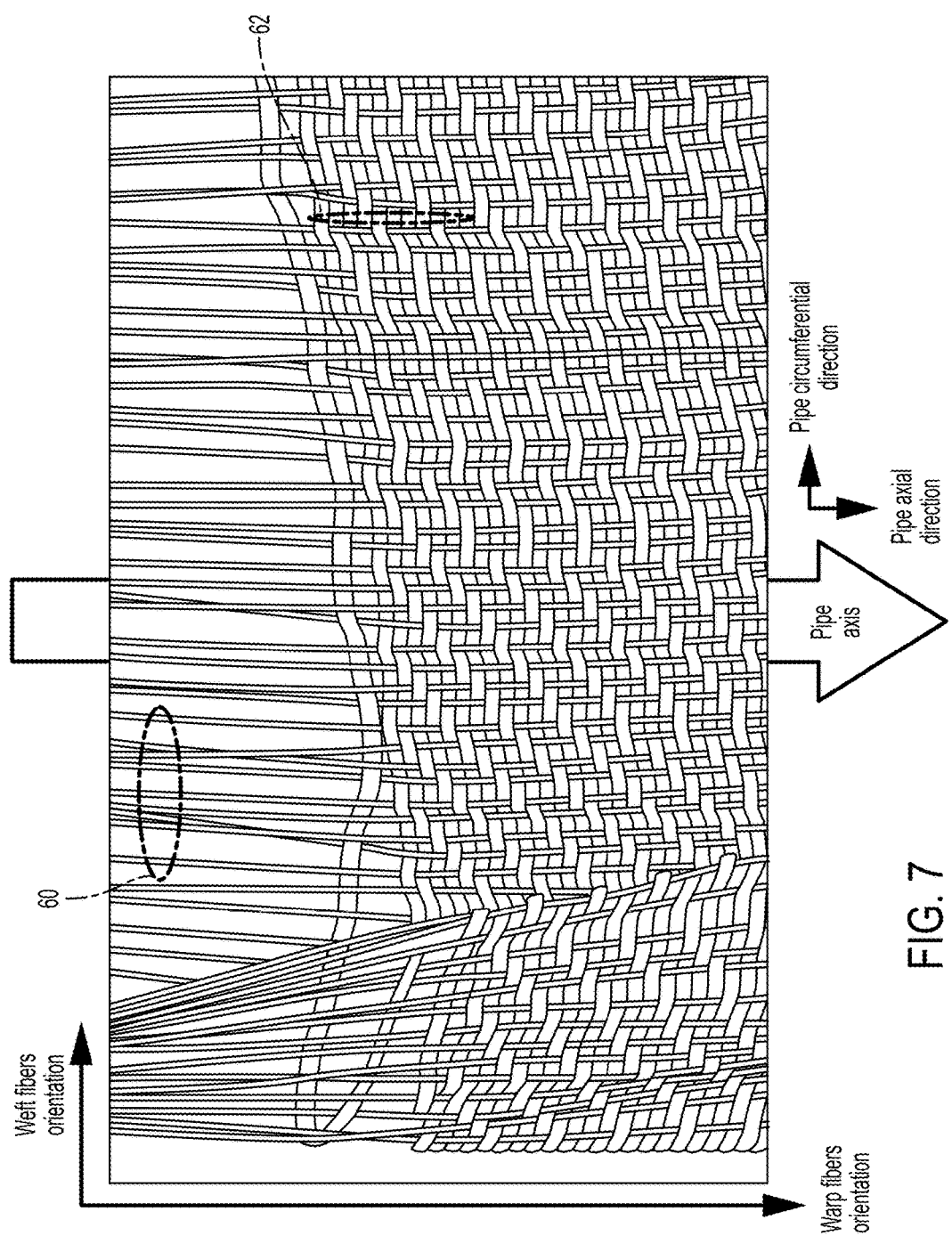

With reference to FIGS. 6 and 7, the opposing considerations of inelasticity for accurate axial encoding versus elasticity to accommodate pipe bends and welds is naturally accommodated by fibers making up the tubular fabric pipe sheath 22 as follows. The fabric of the tubular fabric pipe sheath 22 includes warp and weft fibers. The warp fibers 60 are arranged to run parallel with the pipe 14 when the tubular fabric pipe sheath 22 is fitted around the outside of the pipe 14. The weft fibers 62 are arranged to run at least partway around the pipe 14 when the tubular fabric pipe sheath 22 is fitted around the outside of the pipe 14. Said another way, the warp fibers 60 run along the tube axis of the tubular fabric pipe sheath 22, while the weft fibers 62 run approximately crosswise to the warp fibers 60 and are woven into the warp fibers 60. The warp fibers 60 are inelastic so as to avoid axial stretching of the tubular fabric pipe sheath 22 as it is moved to draw the scanner collar 20 inboard. On the other hand, the weft fibers 62 are elastic so as to enable the tubular fabric pipe sheath 22 to accommodate pipe bends, pipe welds, and the like. In general, the weft fibers 62 are more elastic than the warp fibers 60. A side benefit of this fabric design is that the inelastic warp fibers 60 tend to suppress rotation of the scanner collar 20 as it is drawn inboard via the tubular fabric pipe sheath 22.

In sum, the fabric of the tubular fabric pipe sheath 22 preferably is strong and stretch-free (i.e. inelastic) on the warp direction which is axially aligned with the pipe 14 to be inspected. Materials such as Dyneema, Vectran, Kevlar, or so forth are contemplated for the warp fibers 60. The weft fibers 62 are suitably made of a stretch yarn like Spandex or another elastic fiber material, so that the encircling weave (that is, the weft 62) can expand over field welds in the pipe bends, accommodate variations in tube ovality, the like. One contemplated fabric is a warp surfaced twill with Dyneema warp fibers, which is expected to reduce friction on the feeder pipe 14 by presenting the relatively slick Dyneema warp fibers to the feeder outer diameter (OD) surface.

While in the illustrative example the tubular fabric pipe sheath 22 employs a woven fabric with warp and weft fibers as just described, other fabrics are contemplated, including fabrics that do not include warp and weft fibers. In such alternative embodiments, the tubular fabric pipe sheath is preferably constructed of a fabric that is inelastic along the tubular direction and elastic transverse to the tubular direction (or at least which is more elastic transverse to the tubular direction than along the tubular direction). Substantially any type of fabric having anisotropic elasticity can provide this characteristic by aligning the fabric with its inelastic (or less elastic) direction oriented along the pipe axis (i.e. tube axis of the tubular fabric pipe sheath) and with its elastic (or more elastic) direction oriented circumferentially around the pipe. As another contemplated variant, "ripstop" stabilization fibers may be woven in the fabric at certain places at a 45° bias relative to the warp and weft fibers 60, 62 (or, more generally, in a pattern at another angled orientation relative to the warp and weft fibers, and optionally crosshatched). This is analogous to ripstop nylon fabric. The addition of the ripstop fiber pattern tends to prevent rotation around the pipe axis, and enhances reliability of the zipper interface.

An advantage of the disclosed pipe scanning systems as compared with robotic scanners that crawl along the pipe is that the motive force is supplied by a motor (or by hand) at the winch 50; whereas, with a robotic crawler the motive force is supplied by a motor located on-board the robotic crawler. Compared with a robotic crawler, the motor of the winch 50 can be made larger, and additionally is optionally encoded against a fixed location (e.g., the pipe flange 52 based on the length of drawn sheath 22) to provide accurate axial positioning. Another advantage is that only a single motor driving the winch 50 is required (or, alternatively, the winch 50 can be a manually operated reel or pair of reels); whereas, an N-axis robotic crawler typically requires N motors to independently operate the N axes.

The use of the tubular fabric pipe sheath 22 with axial inelasticity and circumferential elasticity suppresses rotation of the scanner collar 20 and can accommodate pipe bends easily as compared with, for example, a winch employing a single draw cable which is likely to become tangled and apply torque forces to the collar. The tubular fabric pipe sheath 22 is also low profile and can draw the scanner collar 20 through areas of small clearance between neighboring pipes.

Figure 8:
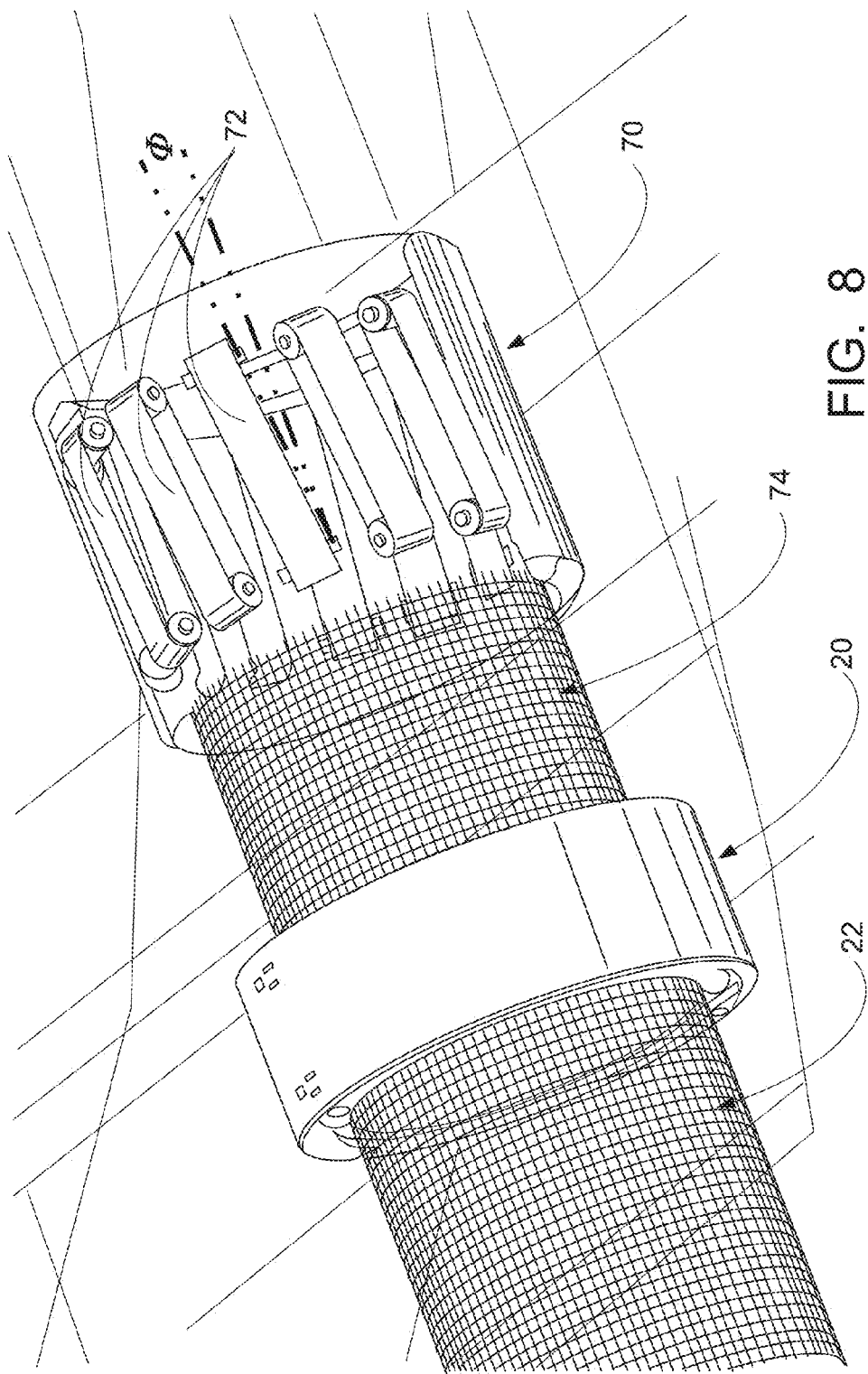
FIGS. 8 and 9 diagrammatically show perspective views with partial transparency of the pipe scanning apparatus of FIGS. 1-4 further including a sanding tool collar attached to the scanner collar by a connecting sleeve.
Figure 9:
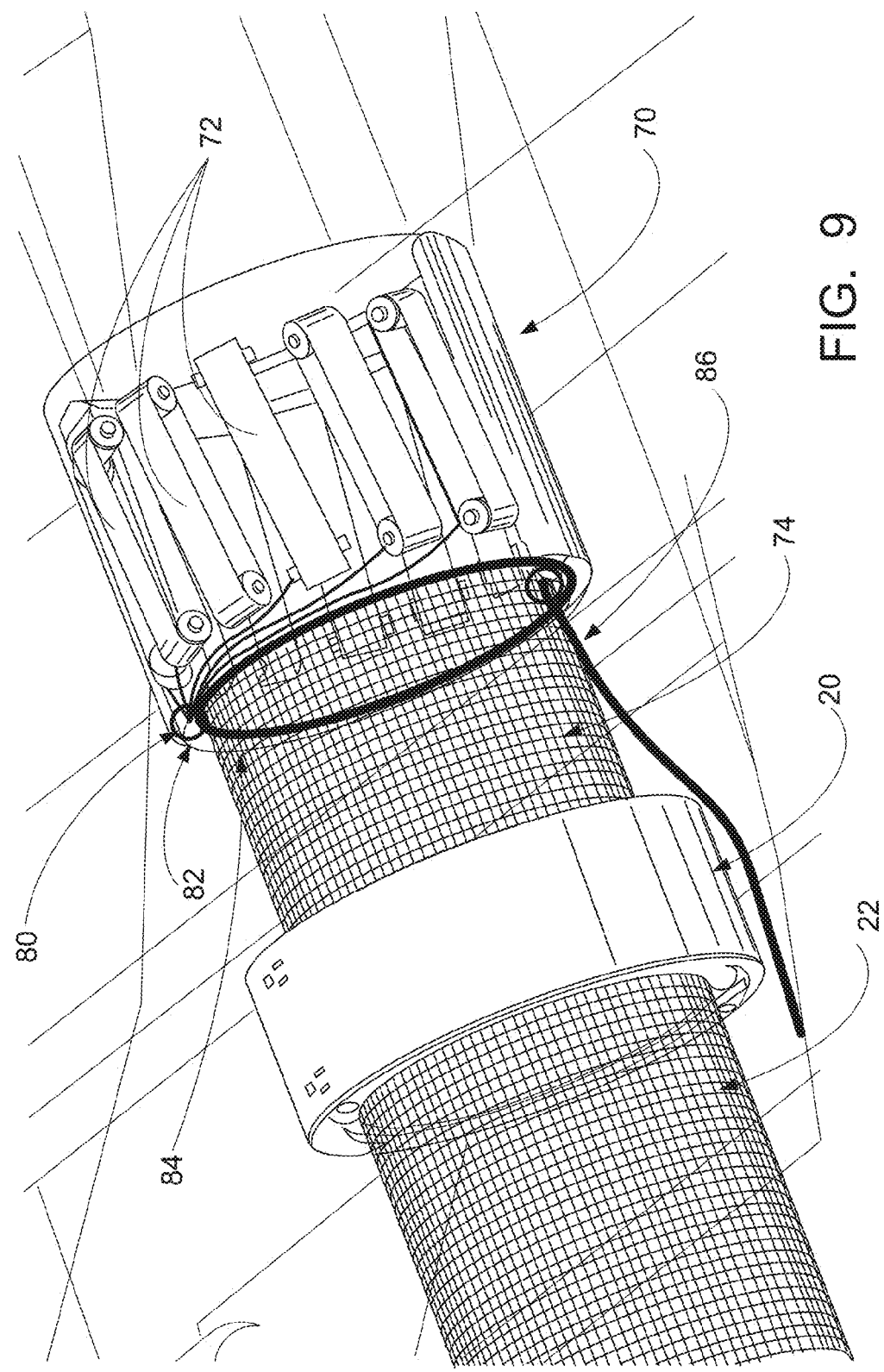
Figure 10:
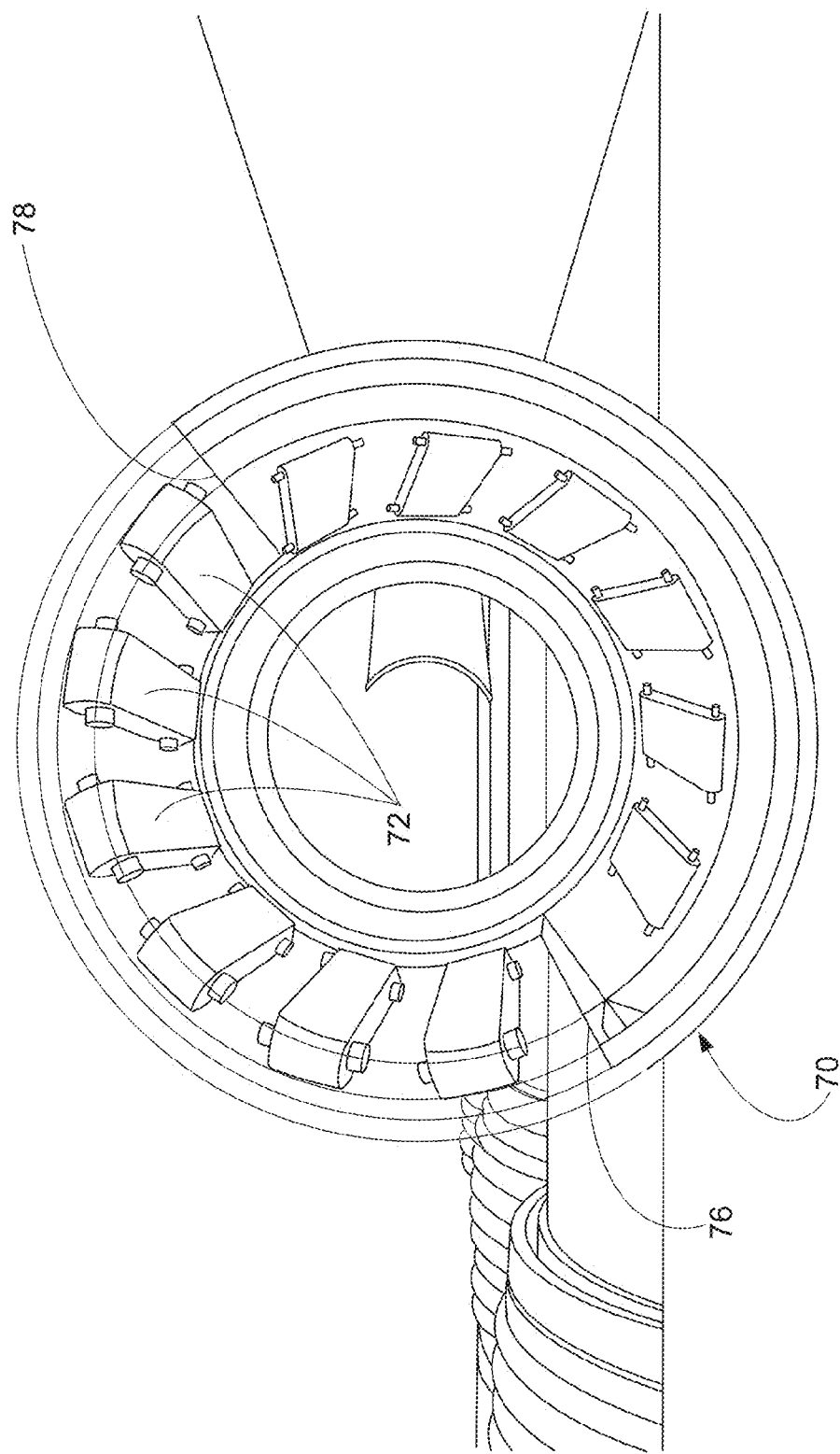
FIG. 10 diagrammatically shows an end view of the sanding tool collar showing its sanding belts.

With reference to FIGS. 8-10, an embodiment is described which includes, in addition to the scanner collar 20, a sanding tool collar 70 containing a set of sanding belts 72. In the illustrative embodiment, the sanding belts 72 are mounted on the sanding tool collar 70 which is separate from the scanner collar 20 and is connected with the scanner collar 20 by a flexible fabric connecting sleeve 74. In a variant embodiment (not shown), the sanding belts are integrated into the scanner collar along with the UT sensors 38, and the scanner collar may be lengthened to accommodate the additional hardware (although the axial extent of the collar may be limited by the need for it to smoothly traverse small-radius pipe bends). The sanding belts 72 provide for sanding the pipe to remove scale, rust, adhered debris, or so forth. This can be useful because in some applications, the tube undergoing ultrasonic testing (UT) preferably has surface scale and rust removed to facilitate accurate UT resolution using the UT Phased Array scanner of the scanner collar 20. As disclosed herein, the sanding belts 72 also optionally provide motive force for performing the operation O2 (see FIG. 5) of moving the scanner collar 20 to the outboard position along the pipe. This approach advantageously leverages the sanding belts 72, which are optionally provided to perform the surface preparation function, to also perform the operation O2.

The illustrative sanding tool collar 70 is of a single hinge clamshell design with a hinge 76 and a clasp 78, and the collar 70 is mounted by opening at the hinge 76, being clamped around the pipe, and securing the clasp 78. In some embodiments the locations of the hinge 76 and clasp 78 are aligned with the slit fasteners 24 of the tubular fabric pipe sheath 22. The detailed clamshell design can take various forms, such as that shown in FIG. 4 for the scanner collar 20. As another contemplated variant, the hinge may be replaced by a second clasp, so that the collar is a two-piece design. The sanding belts 72 are suitably driven by flex shafts 80 driven by drive gearing 82 connected with an outer diameter (OD) gear unit 84 with input flex drive cabling 86 for remote motor power support. The individual sanding belts 72 suitably receive power from the main rotating ring gear 84 in the base of the unit, and individual flex shafts 80 are pulled from the main gear 84 to the individual sanding belts 72. In some applications, space constraints on the sanding tool collar 70 do not allow for a motor large enough to do the sanding work to be carried along on the collar 70, hence the use of external power via the cabling 86 and flex shaft system 80, 82, 84. For example, in the illustrative CANDU reactor feeder tube inspection task, the radial clearance is around 10 mm away from the surface of the feeder tube or less. Each sanding belt 72 may have separately adjustable tension along the circumference of the belt and normal to the pipe surface using screw locking systems (not shown). The sanding belts 72 are suitably fabricated and spliced to length using fiber reinforced tape cut on a scarf joint angle (e.g., 15-25 degrees from a perfect square cut).

To achieve 360° circumferential sanding coverage, a rotational stage may be added to the sanding tool collar 70 before the attachment of the flex shaft 86 to allow for the collar 70 to spin. In some embodiments controlled rotation of the collar 70 is achieved by a dual flex shaft drive, with right hand helix belts set with a higher normal force with respect to the pipe than the left hand helix belts (or vice versa), so as to obtain a constant spin of the collar 70 accomplished by differential frictions of the left and right helix belts. In a suitable arrangement, a stationary rear bearing system (not shown) may be employed that stays stationary while the main body of the sanding tool spins around the pipe. The OD gear unit 84 is mounted on the stationary portion, and the spinning main body is attached through the bearing 84 to the stationary portion. This approach allows the spinning without affecting the connection of the sanding tool collar 70 to the fabric sleeve 74. Stabilization wheels may be provided to prevent transmission of bleed torque back into the fabric system.

In another approach, the sanding tool collar 70 does not spin during operation, but instead the number, width, and other parameters of the sanding belts 72 are chosen to provide full 360° circumferential sanding of the pipe. One approach to facilitate complete circumferential coverage is to cant the sanding belts 72 at an angle $\phi$ as indicated in FIG. 8, to increase the overlap between neighboring sanding belts and create an overlapping pattern in the sanding belt systems. Patens may be added to the inner diameter (ID) of the belt to ensure that all areas of the belt sanding area receive approximately equal force from the belts.

Figure 11:
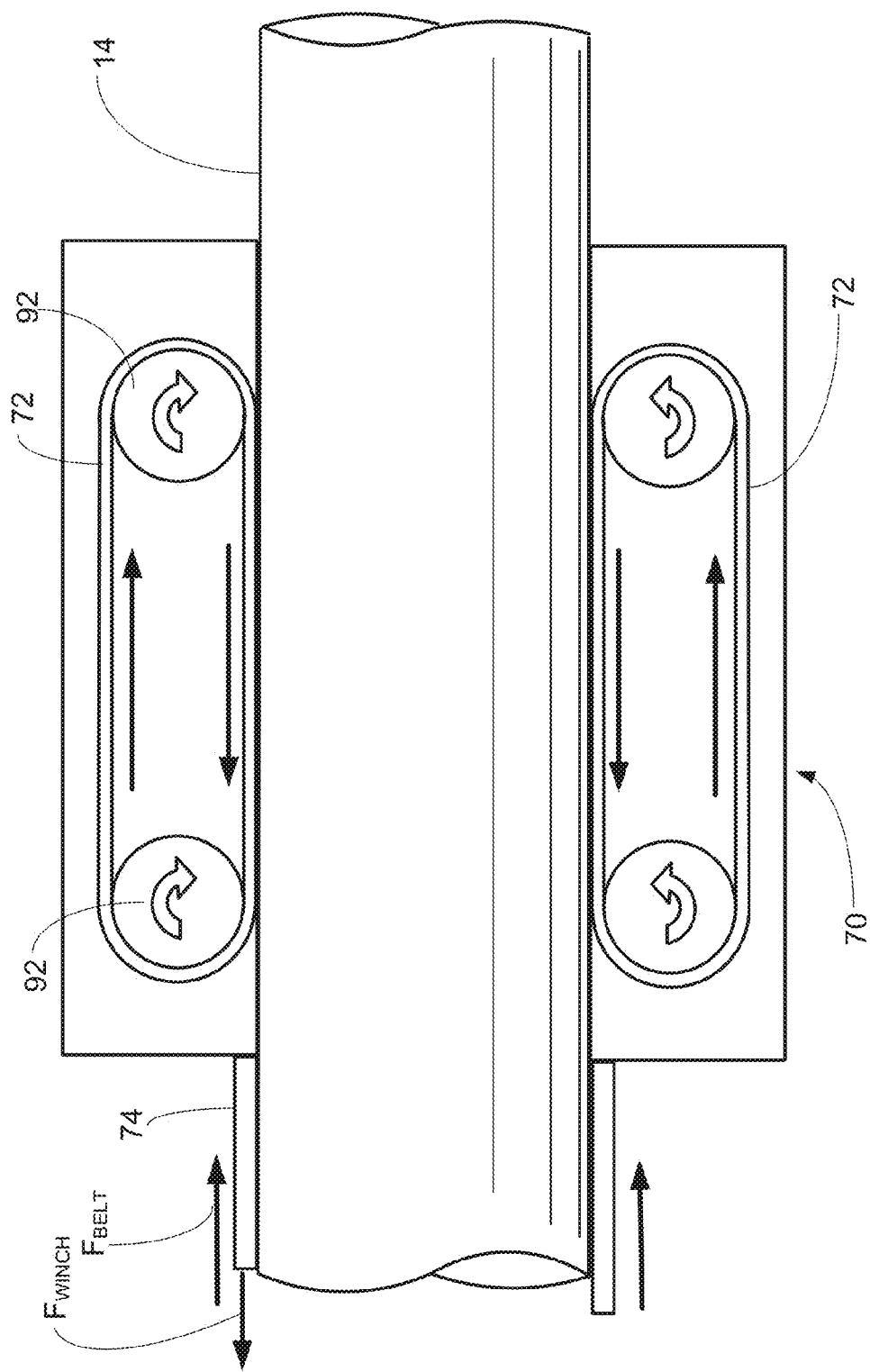
FIG. 11 diagrammatically shows a side sectional view of the sanding tool collar of FIGS. 8-10 with opposing forces generated by the sanding belts and the winch indicated.

With reference to FIG. 11, the use of the sanding tool collar 70 to move the scanner collar 20 to the outboard position is illustrated. In FIG. 11, the inboard position is to the left and the outboard position is to the right. If the sanding belts 72 are all rotating in the same direction, as shown in FIG. 11, then they act against the feeder pipe 14 to move the sanding tool collar 70 to the right (in FIG. 11), that is, in the outboard direction. This imparts a force $F_{belt}$ on the connecting sleeve 74 and hence on the scanner collar 20 (see FIGS. 8 and 9), which drives the scanner collar 20 in the outboard direction. However, to accomplish the sanding task, it is necessary that the sanding belts 72 slide along the surface of the feeder pipe 14, so as to abrasively engage the pipe surface and perform sanding. To this end, the winch 50 may be operated to produce a counterforce $F_{winch}$ on the connecting sleeve 74 that opposes the belt force $F_{belt}$. By appropriate adjustment of force applied by the winch 50 so that $F_{belt} > F_{winch}$, the effect is to perform sanding while controllably moving the sanding tool collar 70 and the attached scanner collar 20 in the outboard direction. Thus, the winch 50 is used to restrain the outboard movement of the sanding tool collar 70 to ensure it abrasively engages the outer surface of the pipe 14 to perform sanding, and to control the speed of the outboard movement. The combined effect is analogous to a dog on a walk which is straining on the lead. Advantageously, if some length of the pipe requires additional sanding (for example, at a pipe weld), the force $F_{winch}$ can be increased to override the force $F_{belt}$ applied by the sanding belts 72, so that temporarily $F_{winch} > F_{belt}$ and the collars 20, 70 are moved back in the inboard direction past the weld (or other area requiring additional sanding). The winch force $F_{winch}$ is then reduced to its previous level so that $F_{belt} > F_{winch}$ again attained and the is sanded again. This back-and-forth sanding process is optionally repeated more than once to achieve the desired amount of sanding over the weld or other "difficult" pipe region.

If substantial sanding dust is generated by the sanding tool, a vacuum system (not shown) is suitably provided to remove dust and route it for disposal. Advantageously, the vacuum system (e.g., pump, or blower, et cetera) can be located with the winch or at some other convenient location, and connected with the sanding tool collar 70 via a vacuum tube. This provides low clearance. Brushes (not shown) are optionally provided with the sanding tool to ensure that the surface is clean.

To avoid binding of the pull provided by the sander device, the connecting sleeve 74 is optionally configured as a flexible fabric gimbal system that evens out the forces as the sanding tool collar 70 draws the trailing scanner collar 20 around a bend. To this end, the connecting sleeve 74 suitably comprises a combination of flexible and low-stretch fibers, optionally woven in a bias direction mesh to allow some stretch on the extrados of the pipe bend and allow for some collapse around the intrados of the pipe bend. The fabric may suitably be similar to the fabric of the tubular fabric pipe sheath 22, but a bias direction, such as warp and weft oriented at 45°, would allow better stretch and provide a more even towing of the scanner collar 20.

Figure 12:
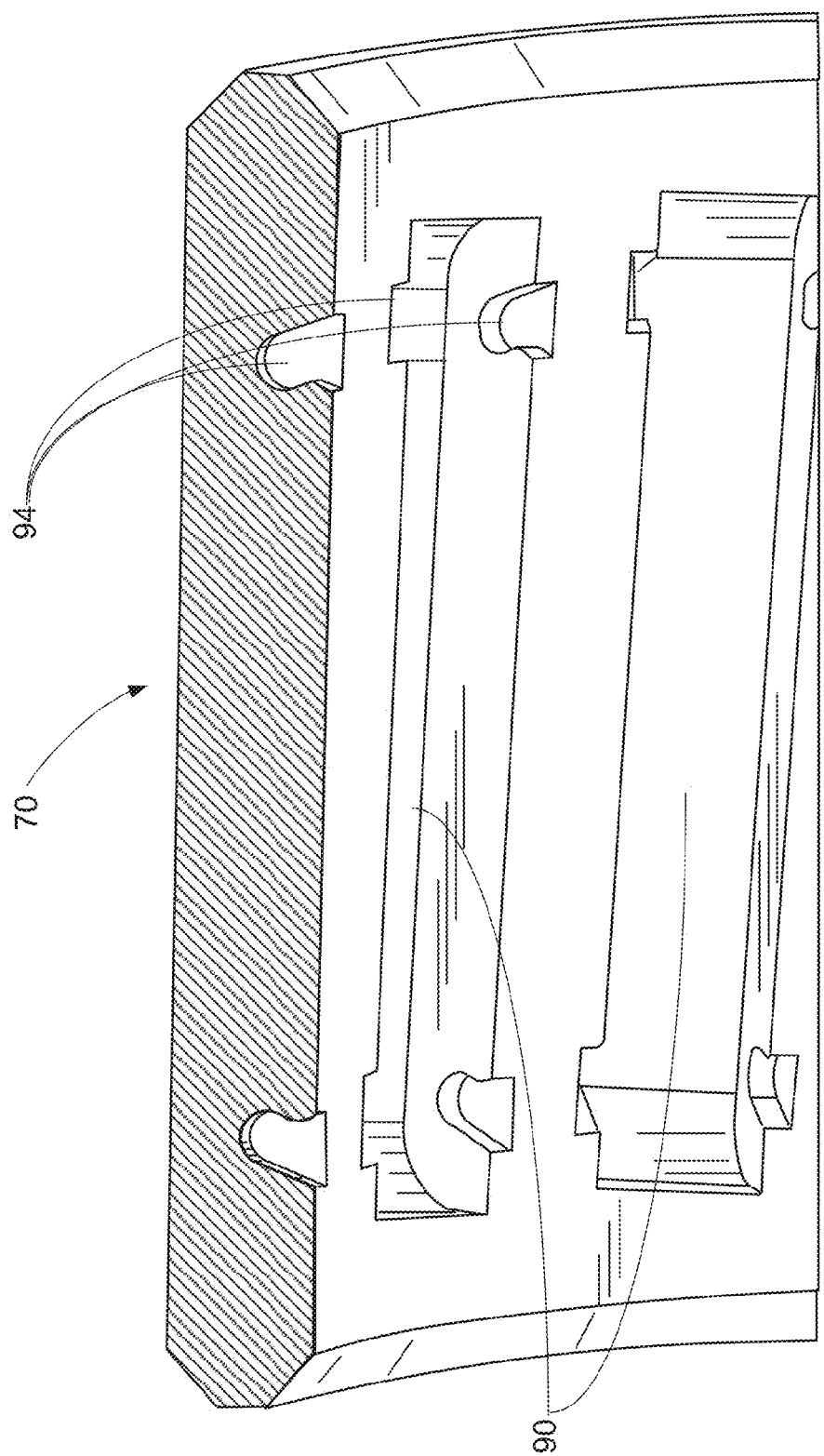
FIG. 12 shows a partial view of the sanding tool collar illustrating suitable receiving slots for receiving the sanding belts.

With reference to FIG. 12, in one embodiment each belt drive is slotted into a receiving slot 90 of the sanding tool collar 70 using a click lock system, with the drive wheel 92 (see FIG. 11) having axial pins engaging receiving slots 94. The drive wheels 92 of the sanding belt 72 may have flat blade style torque pickups to the flex drives, which advantageously simplifies changing of the belts.

Figure 13:
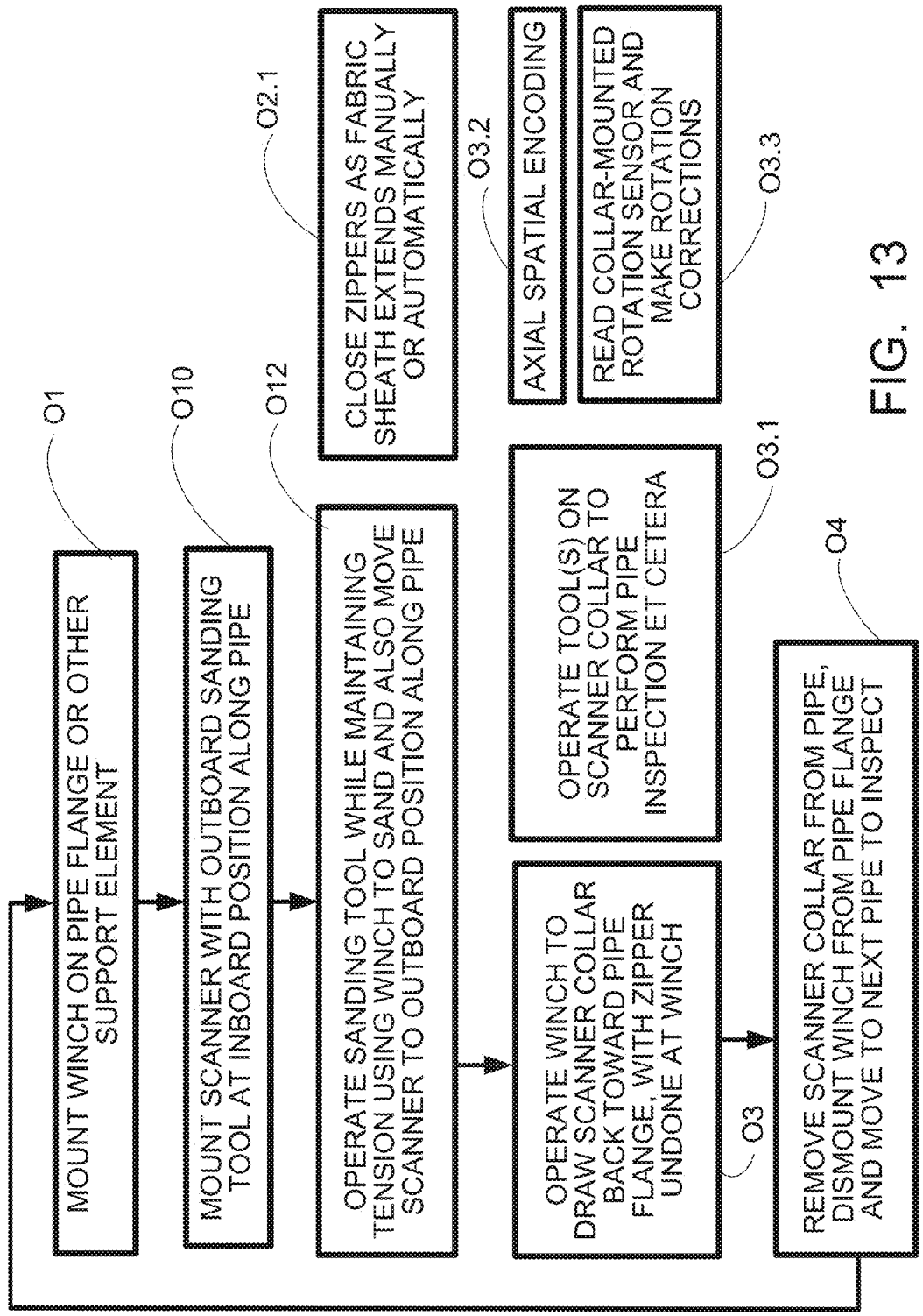
FIG. 13 diagrammatically shows the pipe inspection process of FIG. 5 modified to employ the sanding tool of FIGS. 8-12 to perform the operation of moving the scanner collar to its outboard position.

With reference to FIG. 13, the system operation shown in FIG. 5 is modified when using the sanding tool of FIGS. 8-12 as follows. The operation O2 of moving the scanner collar 20 to its outboard position is replaced by an operation O10 in which the scanner collar 20 and the sanding tool collar 70 are mounted at the inboard position along the pipe, with the sanding tool collar 70 located outboard of the scanner collar 20. In an operation O12, the sanding tool is operated which automatically moves the scanner collar 20 in the outboard direction by way of the force $F_{belt}$ as described with reference to FIG. 11, while maintaining suitable tension by way of the counterforce $F_{winch}$ applied by the winch 50 as also described with reference to FIG. 11. During this outboard movement, the zippers are closed in the operation O2.1 as already described with reference to FIG. 5. When the scanner collar 20 reaches its outboard position, the method transitions to operation O3 and following which are performed as already described with reference to FIG. 5.

As previously noted, the Candu® reactor feeder tube inspection task is merely an illustrative example. More generally, the disclosed pipe scanning apparatus and methods can be employed for any type of pipe inspection or processing task, with the tools built into the scanner collar 20 selected for the task at hand. For example, it is contemplated to include pipe processing tools such as a pipe welder, a pipe coater, a pipe sander, or so forth on the scanner collar 20. Various inspection tools may be included, such as UT sensors, radiographic inspection sensors, eddy current inspection sensors, and so forth. The pipe scanning apparatuses disclosed herein are readily applied to scan substantially any type of pipe, including metal pipes, plastic pipes, flexible pipes, rigid pipes, and so forth. A pipe whose diameter varies along its length can be accommodated if the scanner collar 20 is spring-loaded to constrict and expand in accordance with the local pipe diameter.

Illustrative embodiments including the preferred embodiments have been described. While specific embodiments have been shown and described in detail to illustrate the application and principles of the invention and methods, it will be understood that it is not intended that the present invention be limited thereto and that the invention may be embodied otherwise without departing from such principles. In some embodiments of the invention, certain features of the invention may sometimes be used to advantage without a corresponding use of the other features. Accordingly, all such changes and embodiments properly fall within the scope of the following claims. Obviously, modifications and alterations will occur to others upon reading and understanding the preceding detailed description. It is intended that the present disclosure be construed as including all such modifications and alterations insofar as they come within the scope of the appended claims or the equivalents thereof.

I claim:

1. An apparatus for scanning a pipe, the apparatus comprising:
   a scanner collar sized to fit around the outside of the pipe and including tools configured to inspect or modify the pipe, wherein the tools of the scanner collar configured to inspect or modify the pipe include one or more of: ultrasonic testing (UT) sensors, radiographic inspection sensors, eddy current inspection sensors, a pipe welding tool, a pipe surface coating tool, and a pipe sanding tool;
   a tubular fabric pipe sheath sized to fit around the outside of the pipe and connected at an end to the scanner collar; and
   a powered winch or manually operable reel configured to draw in the tubular fabric pipe sheath so as to scan the scanner collar connected to the end of the tubular fabric pipe sheath over the pipe.

2. The apparatus of claim 1, wherein the tubular fabric pipe sheath comprises:
   warp fibers arranged to run parallel with the pipe when the tubular fabric pipe sheath is fitted around the outside of the pipe; and
   weft fibers arranged to run at least partway around the pipe when the tubular fabric pipe sheath is fitted around the outside of the pipe.

3. The apparatus of claim 2, wherein the weft fibers are more elastic than the warp fibers.

4. The apparatus of claim 1, wherein the tubular fabric pipe sheath is inelastic in its axial direction and elastic in its circumferential direction.

5. The apparatus of claim 1, wherein the tubular fabric pipe sheath includes one or more longitudinal slits with slit fasteners.

6. The apparatus of claim 5, wherein the apparatus further comprises:
   an unfastening element disposed with the powered winch or manually operable reel, the unfastening element configured to open the one or more slit fasteners as the tubular fabric pipe sheath is drawn into the powered winch or manually operable reel.

7. The apparatus of claim 1, further comprising:
   sanding belts configured to sand the outside of the pipe;
   wherein the rotational direction of the sanding belts is effective to apply a force to the scanner collar in a direction opposite the drawing force applied by the powered winch or manually operable reel.

8. The apparatus of claim 7, further comprising:
   a sanding tool collar on which the sanding belts are disposed; and
   a flexible fabric connecting sleeve connecting the scanner collar and the sanding tool collar.

9. An apparatus for scanning a pipe, the apparatus comprising:
   a scanner collar sized to fit around the outside of the pipe and including tools configured to inspect or modify the pipe, wherein the tools of the scanner collar configured to inspect or modify the pipe include one or more of: ultrasonic testing (UT) sensors, radiographic inspection sensors, eddy current inspection sensors, a pipe welding tool, a pipe surface coating tool, and a pipe sanding tool; and
   a tubular fabric pipe sheath sized to fit around the outside of the pipe and connected at an end to the scanner collar, the tubular fabric pipe sheath including warp and weft fibers wherein the warp fibers run along the tube axis of the tubular fabric pipe sheath, the tubular fabric pipe sheath further including at least one longitudinal slit having a slit fastener.

10. The apparatus of claim 9, wherein the weft fibers are more elastic than the warp fibers.

11. The apparatus of claim 9, wherein the warp fibers are inelastic and the weft fibers are elastic.

12. The apparatus of claim 9, wherein the tubular fabric pipe sheath includes two said longitudinal slits on opposite sides of the tubular fabric pipe sheath whereby the tubular fabric pipe sheath is separable into two sheath halves.

13. The apparatus of claim 9, further comprising:
   a powered winch or manually operable reel configured to draw in the tubular fabric pipe sheath so as to scan the scanner collar connected to the end of the tubular fabric pipe sheath over the pipe.

14. The apparatus of claim 9, wherein the tubular fabric pipe sheath includes a ripstop fiber pattern comprising fibers at an angled orientation relative to the warp and weft fibers.

15. The apparatus of claim 14, wherein the ripstop fiber pattern is oriented at 45° relative to the warp and weft fibers.

16. The apparatus of claim 14, wherein the ripstop fiber pattern is a crosshatched pattern at an angled orientation relative to the warp and weft fibers.

17. A method for scanning a pipe, the method comprising:
   moving a scanner collar secured around the outside of the pipe to an outboard position, the moving causing a tubular fabric pipe sheath connected to the scanner collar to extend and sheath the pipe up to the outboard position of the scanner collar;
   drawing the tubular fabric pipe sheath inward, the drawing causing the scanner collar to move inward from its initial outboard position;
   and during the drawing, operating tools disposed on the scanner collar to inspect or modify the pipe, wherein the tools of the scanner collar configured to inspect or modify the pipe include one or more of: ultrasonic testing (UT) sensors, radiographic inspection sensors, eddy current inspection sensors, a pipe welding tool, a pipe surface coating tool, and a pipe sanding tool.

18. The method of claim 17, wherein the drawing comprises:
   drawing the tubular fabric pipe sheath using a powered winch or manually operable reel; and
   as the tubular fabric pipe sheath reaches the powered winch or manually operable reel, separating one or more longitudinal seams of the tubular fabric pipe sheath to disengage the tubular fabric pipe sheath from the pipe.

19. The method of claim 17, wherein the drawing comprises:
keeping the tubular fabric pipe sheath taut along the axis of the pipe using inelastic warp fibers oriented along the tube axis of the tubular fabric pipe sheath; and
allowing the tubular fabric pipe sheath to expand and contract circumferentially around the pipe using elastic weft fibers of the tubular fabric pipe sheath.

20. The method of claim 17, wherein the method does not include accessing the interior of the pipe.

21. The method of claim 17, wherein the moving comprises:
operating sanding belts mounted on or with the scanner collar to sand the outside of the pipe, the engagement of the sanding belts with the outside of the pipe also moving the scanner collar toward the outboard position.

22. The method of claim 21, wherein the sanding belts are mounted on a sanding tool collar connected with the scanner collar by a connecting sleeve, and the engagement of the sanding belts with the outside of the pipe moves the scanner collar toward the outboard position by pulling on the scanner collar via the connecting sleeve.

23. The method of claim 21, wherein the drawing comprises drawing the tubular fabric pipe sheath using a powered winch or manually operable reel, and the method further comprises:
during the moving, operating the powered winch or manually operable reel to apply a counterforce to the scanner collar that opposes the movement of the scanner collar toward the outboard position.

24. The method of claim 23, wherein operating the powered winch or manually operable reel to apply a counterforce includes:
adjusting the counterforce applied by the powered winch or manually operable reel to control the rate of movement of the scanner collar toward the outboard position.

25. The method of claim 17, wherein the drawing comprises:
drawing the tubular fabric pipe sheath using a powered winch or manually operable reel; and
during the drawing, measuring a movement rate or displacement of the scanning collar using one or more of (i) an axial position sensor mounted on the scanning collar and observing the pipe, (ii) an axial position sensor mounted proximate to the powered winch or manually operable reel observing the fabric as it is taken up by the powered winch or manually operable reel, and (iii) a rotary encoder mounted on a spool of the powered winch or manually operable reel or on an in-feed roller associated with the powered winch or manually operable reel.

* * * * *